United States Patent [19]

Arakawa

[11] Patent Number: 4,646,723
[45] Date of Patent: Mar. 3, 1987

[54] CONSTRUCTION OF A FORWARD END PORTION OF AN ENDOSCOPE USING A HEAT CONDUCTIVE MATERIAL

[75] Inventor: Satoshi Arakawa, Omiya, Japan
[73] Assignee: Fuji Photo Optical Co., Ltd., Japan
[21] Appl. No.: 766,801
[22] Filed: Aug. 19, 1985
[30] Foreign Application Priority Data
Aug. 23, 1984 [JP] Japan .............. 59-127934[U]
[51] Int. Cl.[4] .............................................. A61B 1/06
[52] U.S. Cl. ........................................ 128/6; 165/185
[58] Field of Search ............... 128/4, 6, 7, 8; 358/98; 165/185

[56] References Cited

U.S. PATENT DOCUMENTS 4,573,450  3/1986  Arakawa ................................ 128/6
4,574,879  3/1986  DeGree et al. ..................... 165/185

FOREIGN PATENT DOCUMENTS 51119532  4/1978  Japan .

Primary Examiner—William H. Grieb
Attorney, Agent, or Firm—Parkhurst & Oliff

[57] ABSTRACT

An endoscope is provided which includes a viewing head in a section which is insertable into a cavity of a living body. An image sensor for generating a video signal which in turn is transmitted to a television display to be visualized thereon as a television picture is provided in the viewing head. The image sensor with a shape such as a plate is located in a plane containing the longitudinal center line of the viewing head. A heat conductive material is provided in a space formed between a metal barrel of the insertable section and the plate-shaped image sensor provided in the metal barrel. With this arrangement, heat accumulated in the image sensor can be emitted to the outside.

3 Claims, 2 Drawing Figures

CONSTRUCTION OF A FORWARD END PORTION OF AN ENDOSCOPE USING A HEAT CONDUCTIVE MATERIAL

BACKGROUND OF THE INVENTION

1. Field of the Invention

The present invention relates to an endoscope, and more particularly relates to an endoscope which has an image pick-up device a plate like image sensor disposed within a viewing head thereof.

2. Description of the Prior Art

In addition to endoscopes having an optical fiber bundle as its image guide means, TV endoscopes have been proposed which have an image sensor as an image pick-up device such as a charge coupled device (CCD) which comprises a great number of small photosensitive elements (pixels) arranged in matrix. Such TV endoscopes which are far better than endoscopes heretofore used from the standpoint of durability, the effect of video signal managment and production costs, are in the improvement stage for practical application.

Now, an image sensor such as, for example, a CCD (charge coupled device) used as the forward end imaging device of the TV endoscope is comprised of a semiconductor and the intrinsic characteristics thereof tend to make it difficult to function under high temperature. More specifically, in view of the temperature characteristics of the CCD, dark current is increased in value under the igh temperature of about 40° C., whereby the noises due to this dark current are increased to a considerable extent, so that the S/N (Signal/Noise) ratio is decreased.

Consequently, heat accumulation at a forward end portion of an insertable flexible section of the endoscope from the body temperature when a cavity of a living body is observed and heat generation by the image sensor itself exert adverse influences on the image pick-up. Because of this, there have been various proposals made including providing a special cooling device in the forward end portion of the endoscope. However, the provision of the special cooling device presents the disadvantages of complicating the construction of the forward end portion of the endoscope and increasing the size of the forward end.

SUMMARY OF THE INVENTION

The present invention was developed to obviate the above-described disadvantages of the prior art. It is accordingly an object of the present invention to provide an endoscope wherein heat accumulated in an image sensor can be emitted to the outside with a simple construction to thereby obtain an accurate image.

The endoscope according to the present invention is of such an arrangement that an image sensor is connected to a metal barrel of the flexible insertable section through a heat conductive material. With this arrangement, heat accumulated in the image sensor is transferred to the metal barrel through the heat conductive material and emitted from the metal barrel to the outside, i.e., to the interior of a cavity of a living body, to thereby prevent the image sensor from being heated to a high temperature.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts through the figures thereof and wherein.

DETAILED DESCRIPTION OF THE PREFERRED EMBODIMENT

Description will hereunder be given of the preferred embodiment of an endoscope according to the present invention with reference to the accompanying drawings.

Figure 1:
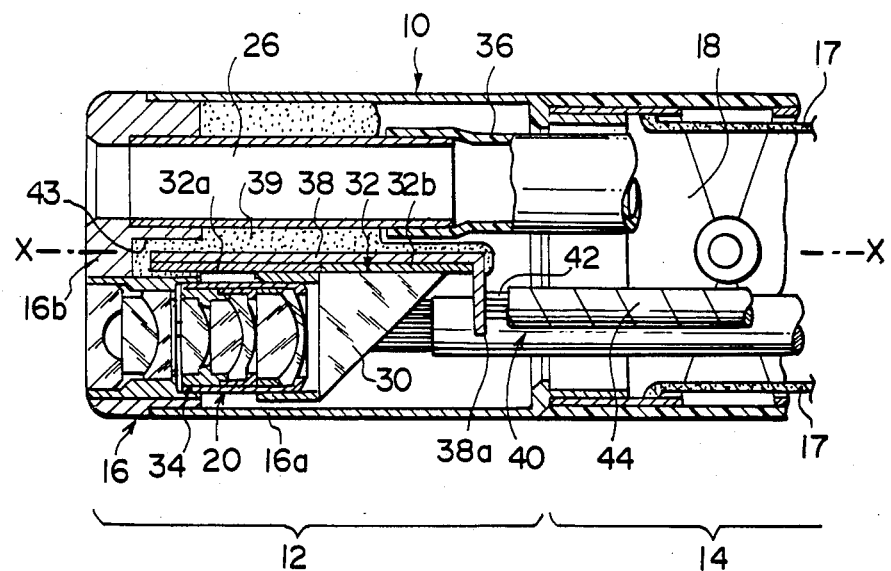
FIG. 1 is a longitudinal sectional view of an embodiment in which the present invention is applied to a front view type of endoscope.
Figure 2:
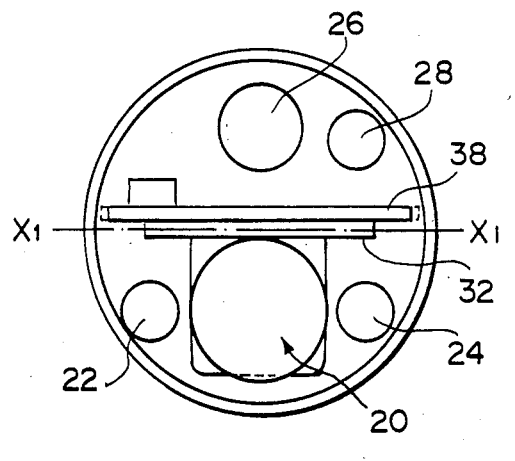
FIG. 2 is a schematic cross sectional view of the endoscope shown in FIG. 1.

Referring now to drawings, shown therein in sectional form, is an embodiment in which the present invention is applied to a front view type of endoscope having a flexible section insertable into a cavity of a living body including in its forward end portion 10 a viewing head 12 and intermediate bendable part 14. The viewing head 12, which has a metal barrel 16, is unflexible. This metal barrel 16 is comprised of a tubular metal 16a forming a main portion of the viewing body 12 and disc-shaped forward end portion 16b coupled to the forward end of the tubular metal 16a. The bending part 14, comprises a chain of rings 18 articulated to one another which is flexed in desired directions by the flexing controlling wires (not shown) in a manner well known in the art. As seen from FIG. 2, various elements are incorporated within the forward end portion 10 such as light guide means 22 and 24, a forceps channel 26 and an air and water supply channel 28 as well as an objective lens assembly 20. Each element extends along the longitudinal axis of the flexible section (that is, the horizontal direction in FIG. 1). As apparent from FIG. 1, in the rear of the objective lens assembly 20 generally comprising plural elements, a right-angled prism 30 is provided for turning the optical axis of the objective lens assembly 20 at a right angle. The prism 30 has a light emitting surface to which a plate like, rectangular image sensor 32 is cemented.

The above arrangement of the image pick-up unit permits the image sensor plate 32 to be located close to a plane containing the center line (shown by the line X—X in FIG. 1 and XI—XI in FIG. 2), making it possible to use the limited space effectively. It should be noted that if a dustproof construction is not required, it is not always necessary to cement the image sensor plate 32 to the prism 30. Therefore, elements, for example a lens, a masking member and the like, may be disposed therebetween. In addition, a reflection mirror disposed at about a right angle may be substituted for the prism 30.

Various channels are provided in the forward end portion 16b of the metal barrel 16, for example a forceps channel 26 coupled to a guide tube 36 through which forceps are inserted into a cavity. As apparent from FIGS. 1 and 2, a seating plate 38 to which the image sensor plate 32 is fixed has a width (in the direction of a diameter of the metal barrel) slightly greater than the width of the image sensor plate and a length (in the longitudinal direction of the metal barrel) substantially equal to the length of the image sensor.)

A rear end portion 38a of the seating plate 38 is constructed such that the rear end portion which would have extended rearwardly past the image sensor plate 32 is bent substantially perpendicularly to the axial line of the forward end portion of the flexible section.

Lead wires 40, each one being connected to a single photosensitive element (pixel) of the image sensor, are fixed at their ends to the seating plate 38. As well known in the art, the lead wires 40 serve to transmit driving signals from a control unit (not shown) to the image sensor 32 and video signals generated by the image sensor 32 to the control unit. The lead wires, which are comprised of very thin wires, have a lossened section 42 adjacent to the fixed end of the seating plate and a bundled section 44 covered with a sheath tube.

The lead wires 40 of the image sensor 32 are connected to the rear surface portion of the bent rear end portion 38a of this seating plate 38, with each of the lead wires 40 being connected to a very small photosensitive element of the image sensor 32.

Furthermore, a heat conductive material 39 is interposed between the seating plate 38 of the image sensor 32 and the metal barrel 16. This heat conductive material 39 is obtained by mixing a metal powder such as aluminum with epoxy resin for example. The mixture is placed in a space disposed upwardly of the seating plate 38 in FIG. 1. More specifically, the heat conductive material 39 is filled in the space disposed upwardly of the seating plate 38 and enclosed by the tubular barrel 16a and the disc-shaped forward end portion 16b, and covers the forceps channel 26. In consequence, the seating plate 38 and the metal barrel 16 are thermally connected to each other by the heat conductive material 39 directly, or indirectly through the forceps channel 26 made of a metal, whereby, even when the image sensor 32 and the seating plate 38 are heated by the heat generated by the image sensor 32 itself and by the temperature of the body, the heat is emitted through the metal barrel 16 of the forceps channel 26 to the outside.

In the embodiment of the above-described arrangement of the endoscope according to the present invention, the heat conductive material 39 is interposed between the seating plate 38 of the image sensor and the metal barrel 16, whereby the image sensor is thermally connected to the metal barrel 16, so that the heat accumulated in the image sensor can be emitted to the outside. In consequence, the adverse influence to the image pick-up due to the highly heated image sensor is avoided, so that an accurate image can be obtained.

Moreover, the arrangement is so simple that only the interior of the forward end portion 10 is filled up with the heat conductive material 39, so that the mechanism does not become complicated and large in size and production can be easily carried out.

Additionally, in the above embodiment, the heat conductive material 39 is formed of a mixture of epoxy resin and metal powder (A1 power). However, the present invention need not necessarily be limited to this, and various heat conductive materials can be applied.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope comprising:
    an image sensor and a flexible portion having forward end, said image sensor being located in said forward end, whereby said image sensor produces a video signal which can be used to recreate a picture of an object of interest;
    a tubular metal barrel forming said forward end portion of the endoscope;
    an image sensor plate disposed on a plane which intersects a center axis of said tubular metal barrel, said image sensor being located in the tubular metal barrel; and
    a heat conductive material interposed between said image sensor plate and said tubular metal barrel.

2. An endoscope as set forth in claim 1, wherein said heat conductive material comprises mixture of epoxy resin with aluminum powder.

3. An endoscope as set forth in claim 2, comprising:
    a forceps channel provided in said tubular metal barrel;
    an objective optical system provided in said tubular metal barrel, said forceps channel being partitioned from said optical system by said image sensor plate; and
    a space being formed around said forceps channel, said heat conductive material being provided in said space.

* * * * *